(12) United States Patent
Van Steijn et al.

(10) Patent No.: US 10,244,768 B2
(45) Date of Patent: Apr. 2, 2019

(54) METHOD AND APPARATUS FOR PROCESSING SLAUGHTERED POULTRY

(71) Applicant: Meyn Food Processing Technology B.V.

(72) Inventors: Aloysius Christianus Maria Van Steijn, Oostzaan (NL); Hans Peter Hoste, Oostzaan (NL); Daniël Derksen, Oostzaan (NL)

(73) Assignee: Meyn Food Processing Technology B.V., Oostzaan (NL)

( * ) Notice: Subject to any disclaimer, the term of this patent is extended or adjusted under 35 U.S.C. 154(b) by 0 days.

(21) Appl. No.: 15/474,208

(22) Filed: Mar. 30, 2017

(65) Prior Publication Data
US 2017/0290348 A1  Oct. 12, 2017

(30) Foreign Application Priority Data
Apr. 11, 2016 (NL) .................................. 2016584

(51) Int. Cl.
| | | |
|---|---|---|
| G01N 33/12 | (2006.01) | |
| A22B 5/00 | (2006.01) | |
| A22B 3/00 | (2006.01) | |
| G01N 21/3577 | (2014.01) | |
| G01N 21/359 | (2014.01) | |
| A22C 21/00 | (2006.01) | |

(52) U.S. Cl.
CPC .............. *A22B 5/007* (2013.01); *A22B 3/005* (2013.01); *A22B 5/00* (2013.01); *A22C 21/00* (2013.01); *G01N 21/359* (2013.01); *G01N 21/3577* (2013.01); *G01N 33/12* (2013.01)

(58) Field of Classification Search
CPC ........ A23V 2002/00; A23V 2200/3262; A23V 2200/328; A23V 2250/5118; A23V 2200/304; A23V 2250/21; G01N 21/31; G01N 21/6486; G01N 33/582; G01N 21/65; G01N 33/542; G01N 33/84; G01N 21/255
See application file for complete search history.

(56) References Cited

U.S. PATENT DOCUMENTS

| | | | |
|---|---|---|---|
| 5,980,377 A | 11/1999 | Zwanikken | |
| 6,611,320 B1 * | 8/2003 | Lindberg | ........... A61B 5/14551 356/40 |
| 2003/0065414 A1 | 4/2003 | van den Nieuwelaar | |
| 2013/0029573 A1 * | 1/2013 | Heemskerk | .............. A22B 5/00 452/57 |

OTHER PUBLICATIONS

PCT Search Report NL 2016584 dated Dec. 2, 2016.

\* cited by examiner

*Primary Examiner* — Michael P Stafira
(74) *Attorney, Agent, or Firm* — Dority & Manning, P.A.

(57) ABSTRACT

Method and apparatus for processing slaughtered poultry that is conveyed in a slaughter line of a slaughter house, in order to establish at the start of said slaughter line whether the poultry was alive or dead on arrival at the slaughter house. Such can include the detection of a body parameter of the slaughtered poultry when the poultry is suspended by the legs in the slaughter line after stunning said poultry, and wherein an absorption spectrum of blood of the slaughtered poultry is determined.

23 Claims, 3 Drawing Sheets

METHOD AND APPARATUS FOR PROCESSING SLAUGHTERED POULTRY

PRIORITY STATEMENT

The present application claims priority under 35 U.S.C. § 119 to Dutch Application No. 2016584, filed Apr. 11, 2016.

FIELD OF THE INVENTION

The subject matter of the present disclosure relates generally to a method and apparatus for processing slaughtered poultry.

BACKGROUND OF THE INVENTION

EP-B-0 819 381 discloses a method and apparatus whereby poultry that is transported to the slaughter house is first stunned, then suspended by the legs, and conveyed further down the line for exsanguination, de-feathering, decapitating, visual inspection of the outside, weight determination, evisceration and veterinary inspection of the poultry carcass and viscera before it gets cooled, portioned, and refrigerated. The determination of whether or not poultry has arrived at the slaughter house dead or alive is mentioned in EP-B-0 819 381 as an example in a process which is predominantly concerned with providing a completely, or almost completely automatic performance of inspection tasks. When used for determining whether the poultry was dead or alive on arrival, EP-B-0 819 381 teaches to use temperature measurements for that purpose.

EP 2 534 953 relates to an improved method and system for determining whether the poultry was dead or alive on arrival at the slaughterhouse, also making use of temperature measurements but then at very specific locations.

Current legislation in certain countries on the processing of slaughtered poultry requires that only healthy, alive poultry may be hung in the slaughter line. As is mentioned in the preamble the poultry is suspended by the legs after first being stunned. This makes it difficult to determine whether the poultry was DOA (dead on arrival) or merely stunned, since in both cases the poultry doesn't move. The problem is even more prone in situations that the poultry died shortly before arriving at the slaughterhouse since then rigor mortis has not yet occurred, and the personnel which hangs the birds cannot identify the difference between a stunned bird or a genuine DOA bird.

SUMMARY OF THE INVENTION

The present invention relates to a method of processing slaughtered poultry that is conveyed in a slaughter line of a slaughter house, in order to establish at the start of the slaughter line whether the poultry was alive or dead on arrival at the slaughter house. In certain embodiments, the invention includes detection of a body parameter of the slaughtered poultry when the poultry is suspended by the legs in the slaughter line after stunning of the poultry. The present invention also relates to an apparatus for processing slaughtered poultry. In certain embodiments, the apparatus may include a slaughter line and detection means that are arranged to detect a body parameter of the slaughtered poultry when the poultry is suspended by the legs in the slaughter line after being stunned. Additional aspects and advantages of the invention will be set forth in part in the following description, or may be obvious from the description, or may be learned through practice of the invention.

In one exemplary aspect, it is an object of the invention to further improve the accuracy and reliability of the apparatus and method for processing slaughtered poultry so as to determine whether the poultry arriving at the slaughter line was dead or alive.

A further exemplary object of the invention is to prevent as much as possible the occurrence of false positives—i.e. the determination of poultry being alive on arrival that are deemed to have arrived at the slaughterhouse dead.

Generally speaking it is therefore an exemplary object of the invention to assess the immediate history and status of the suspended poultry.

Still a further exemplary object of the invention is to better monitor the process of killing the poultry in the initial phases of its processing in the processing line. An intention here is to improve animal welfare in the poultry's final life stages.

The invention is embodied in a method and apparatus according to any one of the appended claims.

In a first exemplary aspect of the invention, an absorption spectrum of blood of the slaughtered poultry is determined and based thereon it is decided whether the poultry was alive or dead on arrival at the slaughter house. Accordingly, an exemplary apparatus of the invention can include a slaughter line having means to establish at the start of the slaughter line whether the poultry was alive or dead on arrival at the slaughter line, wherein the means are embodied as detection means that are arranged to determine an absorption spectrum of blood of the slaughtered poultry while the poultry is suspended by the legs.

According to an exemplary aspect, it is preferred that the apparatus and method of the invention are arranged to use the absorption spectrum for determining a level of deoxygenation of the blood of the poultry. This is found to be a reliable measure to distinguish between genuine DOA birds and birds that have been stunned.

To promote the accuracy of the method and apparatus of this exemplary aspect of the invention, it is preferred in certain embodiments that the absorption spectrum is determined for wavelengths between 200 nm and 1000 nm.

Better results can be attainable when the absorption spectrum is determined for wavelengths between 600 nm and 800, and optimal results can be achieved when the absorption spectrum is determined for wavelengths around approximately 680 nm.

To provide reliable results, in certain exemplary embodiments, it is also preferred that stunning of the poultry is executed by controlled atmosphere stunning wherein an atmosphere with depleted oxygen is applied. Such an atmosphere with depleted oxygen is notably provided with excess amounts of carbon dioxide, argon or nitrogen ($N_2$). As a result of this method of stunning the blood is extremely deoxygenated, which makes it easier to distinguish between those stunned birds and DOA birds.

In one exemplary embodiment, an absorption spectrum of blood of the slaughtered poultry is determined of the blood in the arteries and/or in the veins. It is then possible to either determine the absorption spectrum in the arteries or in the veins, or in both the arteries and the veins. This last option may even result in an even more reliable determination of birds being DOA or stunned by looking at a possible difference in the absorption spectra of both the blood in the arteries and of the blood in the veins.

One possible way of making possible to look at the absorption spectra of the blood is initiated in that prior to determining the absorption spectra, at least one of the arteries and/or the veins of the poultry is cut.

In a preferred exemplary embodiment of the method and apparatus of the invention, the absorption spectrum of the blood of the slaughtered poultry is, however, determined noninvasively. This obviates the need that the poultry will be required to actually bleed when it is cut, since cutting is completely avoided in the process of determining DOA birds. This is a big advantage since bleeding of DOA birds is generally impaired depending on the duration of their death. Furthermore it avoids the mess of the blood spilling in the slaughterhouse when the determination of the absorption spectrum of the blood is done noninvasively. To make the measurement noninvasively is particularly advantageous since in modern processing lines the rate of operation is 18,000 birds per hour, and the corresponding swinging of the birds makes cutting a real challenge, not to mention the problems associated with the difference in bleeding rate that different birds may exhibit.

In another exemplary aspect, a preferred position at which the absorption spectrum of the blood of the slaughtered poultry is determined is at non-feathered skin or skin parts of the poultry. The sensitivity of the measurement as well as its reliability is of a high standard at these locations. Best results are achieved when the absorption spectrum of the blood of the slaughtered poultry is determined at one of the wattles of the poultry. More preferable, in certain exemplary embodiments even the absorption spectrum of the blood of the slaughtered poultry is determined at both wattles of the poultry. The wattles are highly perfused with blood, which supports a reliable assessment of the birds being dead on arrival or not. Further as a result of a decreasing contrast between the wattles and the surrounding skin tissue depending on the longevity of the birds being dead, it is also possible to derive information on the conditions prevailing during transport of the poultry to the slaughterhouse. This information can be used to improve animal welfare and to promote a humane slaughtering process.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

The use of identical or similar reference numerals in different figures denotes identical or similar features.

DETAILED DESCRIPTION OF THE INVENTION

For purposes of describing the invention, reference now will be made in detail to embodiments and/or methods of the invention, one or more examples of which are illustrated in or with the drawings. Each example is provided by way of explanation of the invention, not limitation of the invention. In fact, it will be apparent to those skilled in the art that various modifications and variations can be made in the present invention without departing from the scope or spirit of the invention. For instance, features or steps illustrated or described as part of one embodiment, can be used with another embodiment or steps to yield a still further embodiments or methods. Thus, it is intended that the present invention covers such modifications and variations as come within the scope of the appended claims and their equivalents.

Figure 1:
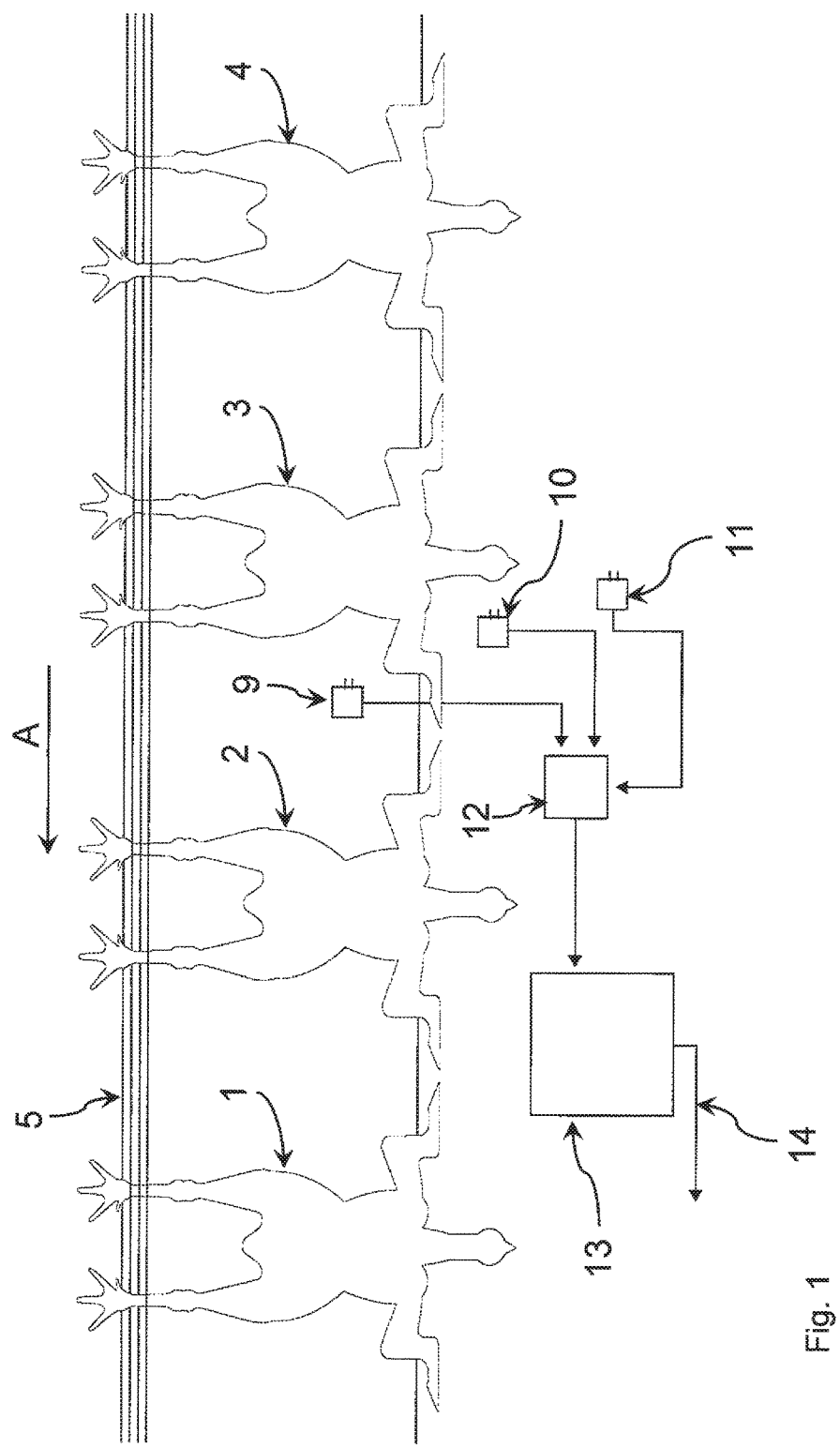
FIG. 1 illustrates an exemplary embodiment of an apparatus of the present invention.

FIG. 1 shows schematically an exemplary processing line for poultry embodied as a suspension conveyor 5 moving in the direction of arrow A. Poultry 1, 2, 3, 4 is suspended by the legs from suspension conveyor 5.

Figure 2:
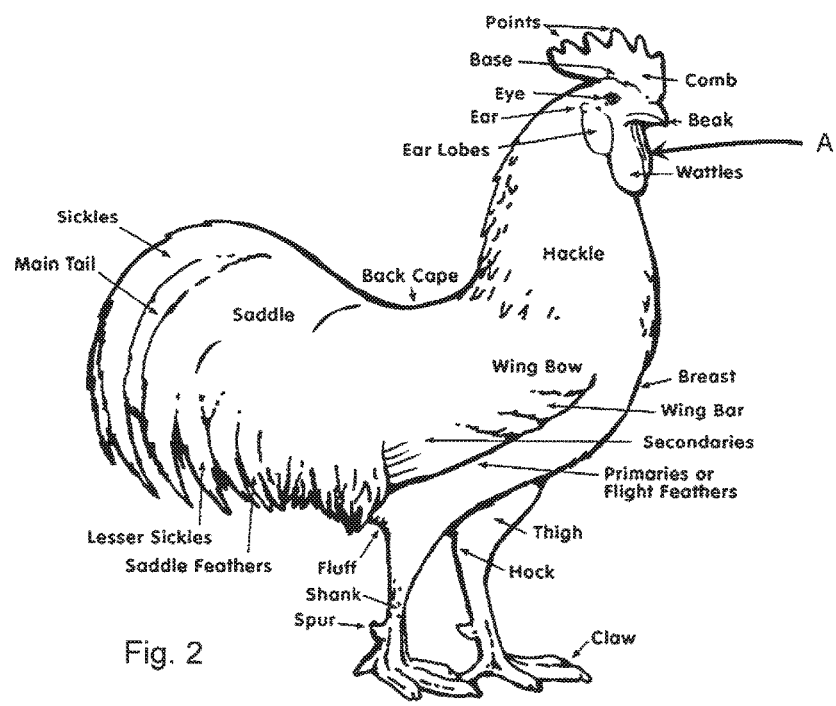
FIG. 2 illustrates an exemplary live chicken.

FIG. 2 illustrates a picture of an exemplary live chicken, which is particularly provided to assist the skilled person to understand the anatomy of poultry, in particular with regard to the location of the wattles near to the poultry's head. The wattles that will be referred to hereinafter are indicated with arrow A.

Turning again to FIG. 1, the exemplary processing line 5 is at the start of the slaughter line provided with exemplary means 9, 10, 11 to establish whether the poultry 1, 2, 3, 4 was alive or dead on arrival at the slaughter line. These means are for that purpose embodied as detection means 9, 10, 11 that are arranged to determine an absorption spectrum of the blood of the slaughtered poultry 1, 2, 3, 4. In FIG. 1, the detection means 9, 10, 11 are provided at several altitudes to take account of poultry with different dimensions. It is however also possible that a single detection means is applied that is tunable in height. In FIG. 1, it is shown that the detection means 10 are specifically arranged to determine the absorption spectrum of the blood of the slaughtered poultry at one of the wattles of the poultry. Preferably, however, the detection means 10 are arranged to determine the absorption spectrum of the blood of the slaughtered poultry at both wattles of the poultry. The location of the wattles is shown in FIG. 2 as explained above.

Other possibilities to determine the absorption spectrum of the blood of the poultry are also feasible, such as e.g., the option that the detection means 9, 10, 11 are arranged to determine an absorption spectrum of the blood in the arteries and/or in the veins of the poultry. In a specific case it then can be opportune that the detection means 9, 10, 11 are arranged to determine a difference in the absorption spectrum with reference to the blood in the arteries and with reference to the blood in the veins. The blood can be made available for the absorption measurement by cutting the arteries and/or the veins of the poultry. Most preferred, however, for this exemplary embodiment is that the detection means 9, 10, 11 as is shown in FIG. 1 are arranged to determine the absorption spectrum of the blood of the slaughtered poultry noninvasively. In one exemplary embodiment, the detection means 9 are arranged to determine the absorption spectrum of the blood of the slaughtered poultry at non-feathered skin or skin parts of the poultry. In another exemplary aspect, the earlier mentioned location for determining the absorption spectrum of the blood at the wattle or wattles of the poultry with detection means 10 is the most preferred option.

FIG. 1 further shows that the detection means 9, 10, 11 connect to calculating means 12 in order to determine a level of deoxygenation of the blood based on the absorption spectrum. The outcome of the calculating means 12 is then used in a control device 13 to establish whether or not the measured poultry 1, 2, 3, 4 was dead or alive on arrival at the slaughter house. Based thereon, the control device 13 may provide an output signal via a line 14 that is used as an actuating signal for a separating device (not shown but known for the person skilled in the art) that is used to release the bird that has been established as being dead on arrival from the conveyor line 5.

Figure 3:
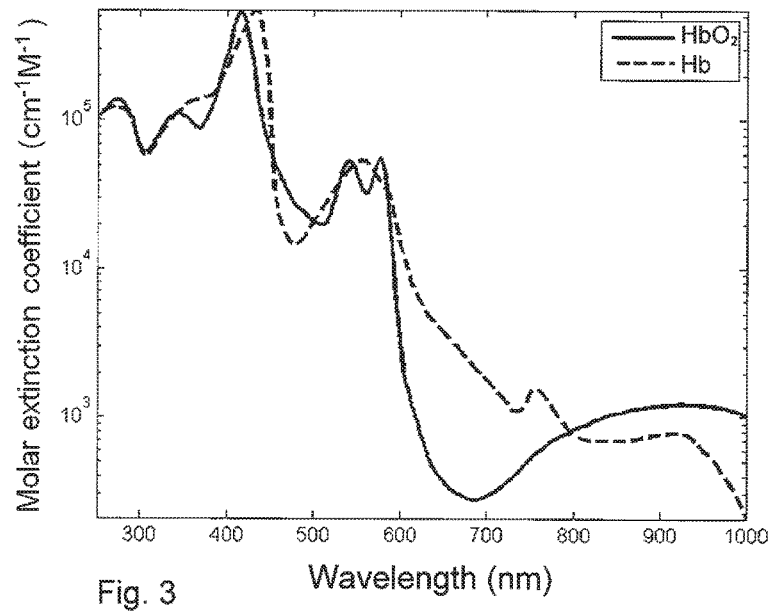
FIG. 3 shows exemplary measurement signals derived with an exemplary method and apparatus of the present invention.

In FIG. 3 a graph is provided representing measurement results at different wavelengths varying between 200 nm and 1000 nanometer, wherein a first graph shows the results with oxygenated blood $HbO_2$, and wherein a second graph shows the results with deoxygenated blood Hb. With reference to these graphs it is preferred according to an exemplary aspect of the invention that the detection means 9, 10, 11 are arranged to determine the absorption spectrum for wavelengths between 200 nm and 1000 nm. In still another exemplary aspect, preferred further options are that the detection means 9, 10, 11 are arranged to determine the absorption spectrum for wavelengths between 600 nm and 800 nm. In yet another exemplary aspect, most preferred is that the detection means 9, 10, 11 are arranged to determine the absorption spectrum for wavelengths around approximately 680 nm.

Figure 4:
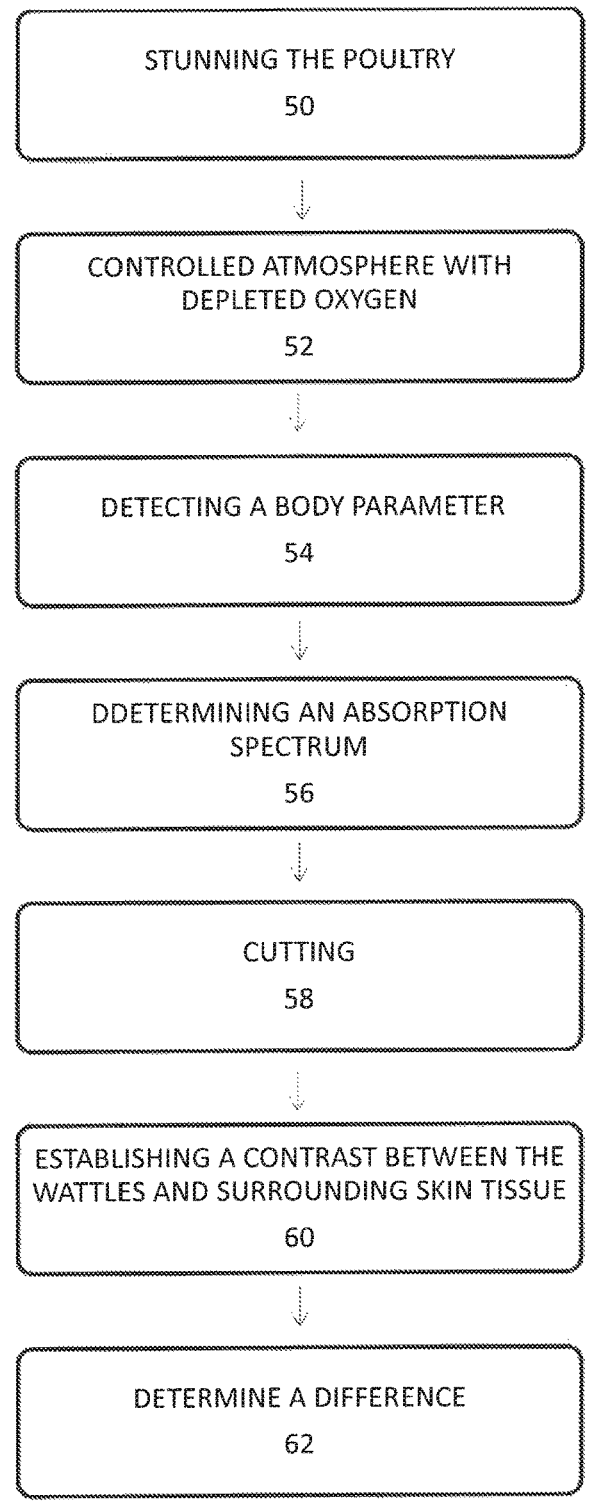
FIG. 4 illustrates an exemplary method of the present invention.

FIG. 4 illustrates an exemplary method of the present invention. In 50, the poultry is stunned. This may include applying to the poultry a controlled atmosphere with depleted oxygen as in 52. A body parameter is detected in 54 and an absorption spectrum is determined in 56. Such may include cutting at least one of the arteries or veins as indicated in 58, may include establishing a contrast between the wattles and surrounding skin tissue as indicated in 60, or may include determining a difference in the aborption spectrum of the blood of the poultry with reference to the blood in the arteries and with reference to blood in the veins as in 62.

Although the invention has been discussed in the foregoing with reference to an exemplary embodiment of the apparatus and method of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

What is claimed is:

1. A method of processing poultry conveyed in a slaughter line of a slaughter house, comprising:
   stunning the poultry;
   obtaining noninvasively at the start of said slaughter line an absorption spectrum of blood of the slaughtered poultry for wavelengths between 200 nm and 1000 nm at non-feathered skin or skin parts of the poultry; and
   determining, from the absorption spectrum, whether the poultry was alive or dead on arrival at the slaughter house by comparing the absorption spectrum of the blood of the slaughtered poultry with absorption spectrum for deoxygenated blood.

2. The method of processing poultry as in claim 1, wherein the absorption spectrum of blood of the slaughtered poultry is determined from blood in the arteries, veins, or both.

3. The method of processing poultry as in claim 1, further comprising determining a difference in the absorption spectrum of blood of the slaughtered poultry with reference to the blood in the arteries and with reference to the blood in the veins.

4. The method of processing poultry as in claim 1, further comprising cutting at least one of the arteries or one of the veins, or both, prior to the determining an absorption spectrum.

5. The method of processing poultry as in claim 1, wherein the blood for the determining, from an absorption spectrum, is from one of the wattles of the poultry.

6. The method of processing poultry as in claim 5, wherein the blood for the determining an absorption spectrum is from both of the wattles of the poultry.

7. The method of processing poultry as in claim 1, wherein the determining an absorption spectrum comprises determining a level of deoxygenation of the blood.

8. The method of processing poultry as in claim 1, wherein the absorption spectrum is determined for wavelengths between 600 nm and 800 nm.

9. The method of processing poultry as in claim 8, wherein the absorption spectrum is determined for wavelengths around approximately 680 nm.

10. The method of processing poultry as in claim 1, wherein the stunning of the poultry is executed by controlled atmosphere wherein an atmosphere where depleted oxygen is applied.

11. The method of processing poultry as in claim 1, further comprising
    establishing a contrast between the wattles and the surrounding skin tissue
    using the contrast to determine the conditions prevailing during transport of the poultry to the slaughterhouse.

12. A method of processing poultry conveyed in a slaughter line of a slaughter house, comprising:
    stunning the poultry;
    obtaining noninvasively at the start of said slaughter line an absorption spectrum of blood of the slaughtered poultry for wavelengths between 200 nm and 1000 nm at non-feathered skin or skin parts of the poultry and
    determining, from the absorption spectrum, whether the poultry was alive or dead on arrival at the slaughter house, wherein the determining comprises ascertaining a level of deoxygenation of the blood of the slaughtered poultry using the absorption spectrum of the blood of the slaughtered poultry and an absorption spectrum for deoxygenated blood.

13. The method of processing poultry as in claim 12, wherein the absorption spectrum of blood of the slaughtered poultry is determined from blood in the arteries, veins, or both.

14. The method of processing poultry as in claim 12, further comprising determining a difference in the absorption spectrum of blood of the slaughtered poultry with reference to the blood in the arteries and with reference to the blood in the veins.

15. The method of processing poultry as in claim 14, wherein the blood for the determining is from both of the wattles of the poultry.

16. The method of processing poultry as in claim 14, wherein the absorption spectrum is determined for wavelengths between 600 nm and 800 nm.

17. The method of processing poultry as in claim 16, wherein the absorption spectrum is determined for wavelengths around approximately 680 nm.

18. The method of processing poultry as in claim 12, further comprising cutting at least one of the arteries or one of the veins, or both, prior to the determining an absorption spectrum.

19. The method of processing poultry as in claim 12, wherein the blood for the determining is from one of the wattles of the poultry.

20. The method of processing poultry as in claim 12, wherein the stunning of the poultry is executed by controlled atmosphere wherein an atmosphere where depleted oxygen is applied.

21. The method of processing poultry as in claim 12, further comprising
- establishing a contrast between the wattles and the surrounding skin tissue
- using the contrast to determine the conditions prevailing during transport of the poultry to the slaughterhouse.

22. The method of processing poultry as in claim 12, further comprising releasing poultry from further conveying in the slaughter line of the level of deoxygenation of the blood of the slaughtered poultry is less than the absorption spectrum for deoxygenated blood.

23. The method of processing poultry as in claim 12, further comprising releasing poultry from further conveying in the slaughter line of the level of deoxygenation of the blood of the slaughtered poultry is less than the absorption spectrum for deoxygenated blood between the wavelengths of 600 nm to 800 nm.

* * * * *